United States Patent
Lamberton et al.

(10) Patent No.: US 9,689,262 B2
(45) Date of Patent: Jun. 27, 2017

(54) THERMOGRAPHIC INSPECTION SYSTEM FOR COMPOSITE WIND TURBINE BLADE

(71) Applicant: General Electric Company, Schenectady, NY (US)

(72) Inventors: Gary Austin Lamberton, Glenville, NY (US); Curtis Wayne Rose, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 1058 days.

(21) Appl. No.: 13/910,178

(22) Filed: Jun. 5, 2013

(65) Prior Publication Data

US 2014/0363294 A1    Dec. 11, 2014

(51) Int. Cl.
| | | |
|---|---|---|
| G01N 25/48 | (2006.01) | |
| F01D 5/12 | (2006.01) | |
| G01N 25/72 | (2006.01) | |

(52) U.S. Cl.
CPC ............. *F01D 5/12* (2013.01); *G01N 25/48* (2013.01); *G01N 25/72* (2013.01); *Y10T 29/49318* (2015.01)

(58) Field of Classification Search
CPC ... B29C 66/91; B29C 66/912; B29C 66/9121; B29C 66/91211; B29C 66/91216; B29C 66/91221; G01N 25/48; G01N 25/72
USPC .......................................................... 156/64
See application file for complete search history.

(56) References Cited

U.S. PATENT DOCUMENTS

| | | |
|---|---|---|
| 3,480,492 A | 11/1969 | Hauser |
| 2003/0038628 A1 | 2/2003 | Nath et al. |
| 2004/0056656 A1 | 3/2004 | McKnight et al. |
| 2005/0169346 A1* | 8/2005 | Murray, Jr. .......... B23K 26/032 374/121 |
| 2008/0219851 A1* | 9/2008 | Althoff ................. F03D 1/0675 416/226 |
| 2009/0108830 A1 | 4/2009 | Rose |
| 2009/0245321 A1 | 10/2009 | Ringermacher et al. |
| 2010/0132137 A1 | 6/2010 | Eggleston |
| 2010/0134098 A1 | 6/2010 | Faidi et al. |
| 2010/0150726 A1 | 6/2010 | Rose et al. |
| 2011/0205348 A1 | 8/2011 | Fritz et al. |
| 2012/0033207 A1 | 2/2012 | Faidi et al. |
| 2012/0310576 A1 | 12/2012 | Rose et al. |
| 2013/0086991 A1 | 4/2013 | Reed et al. |
| 2013/0306217 A1 | 11/2013 | Risko |

FOREIGN PATENT DOCUMENTS

WO        03069324 A1     8/2003

OTHER PUBLICATIONS

European Search Report and Opinion issued in connection with corresponding EP Application No. 14170741.4 on Oct. 31, 2014.

* cited by examiner

*Primary Examiner* — George Koch
(74) *Attorney, Agent, or Firm* — Eversheds Sutherland (US) LLP

(57) ABSTRACT

The present application provides a method of inspecting a bond joint. The method may include the steps of applying an exothermic adhesive to a first shell and/or a second shell, attaching the first shell to the second shell via the exothermic adhesive to create the bond joint, allowing the exothermic adhesive to cure, and imaging the heat released by the exothermic adhesive along the bond joint. The bond joint may be a turbine blade bond joint.

20 Claims, 2 Drawing Sheets

THERMOGRAPHIC INSPECTION SYSTEM FOR COMPOSITE WIND TURBINE BLADE

TECHNICAL FIELD

The present application and resultant patent relate generally to wind turbine blades and inspection systems thereof and more particularly relate to a thermographic inspection system for a composite wind turbine blade bond joint using an exothermic adhesive.

BACKGROUND OF THE INVENTION

Modern wind turbine blades generally combine low weight and low rotational inertia with high rigidity and high resistance to fatigue and wear so as to withstand the various forces and the extreme conditions encountered over a typical life cycle. Generally described, the turbine blades may be formed from two shell halves. A critical step in the manufacture of the turbine blade is the closing of the two shell halves of the blade at a leading edge, a trailing edge, and at a spar cap union with a shear web via an adhesive to create a bond joint. Verifying the width and the overall integrity of this adhesive bond is required to ensure that the turbine blade will meet performance and lifetime requirements. Failure of the turbine blade along the bond joint could lead to significant damage.

Current methods for the inspection of this adhesive bond joint include visual inspection and various types of non-destructive imaging inspection techniques such as ultrasonic testing. Such ultrasonic testing, however, may be time consuming and relatively costly. Moreover, some of the blade materials may be difficult to penetrate via ultrasound. Specifically, certain areas of the blade may be obscured from ultrasonic testing because of the use of foam, balsa, or other types of core materials that may not pass typical ultrasonic frequencies therethrough. Certain types of microwave inspection techniques also are known. Such microwave inspection, however, may be limited by exposure to radiation.

There is thus a desire for improved systems and methods of inspecting an adhesive bond joining the halves of a wind turbine blade. Preferably such systems and methods may accurately and reliably inspect the entire adhesive bond joint without requiring expensive and time consuming ultrasonic testing and the like.

SUMMARY OF THE INVENTION

The present application and the resultant patent thus provide a method of inspecting a bond joint. The method may include the steps of applying an exothermic adhesive to a first shell and/or a second shell, attaching the first shell to the second shell via the exothermic adhesive to create the bond joint, allowing the exothermic adhesive to cure, and imaging the heat released by the exothermic adhesive along the bond joint. The bond joint may be a turbine blade bond joint.

The present application and the resultant patent further provide a turbine blade inspection system. The turbine blade inspection system may include a number of turbine blades with a bond joint of an exothermic adhesive and a thermographic device. The thermographic device may image the heat released by the exothermic adhesive to determine the integrity of the bond joint.

The present application and the resultant patent further provide a turbine blade inspection system. The turbine blade inspection system may include a number of turbine blades with a bond joint of an exothermic adhesive about a first shell and a second shell and an infrared camera. The infrared camera may image the heat released by the exothermic adhesive to determine the integrity of the bond joint.

These and other features and improvements of the present application and the resultant patent will become apparent to one of ordinary skill in the art upon review of the following detailed description when taken in conjunction with the several drawings and the appended claims.

DETAILED DESCRIPTION

Figure 1:
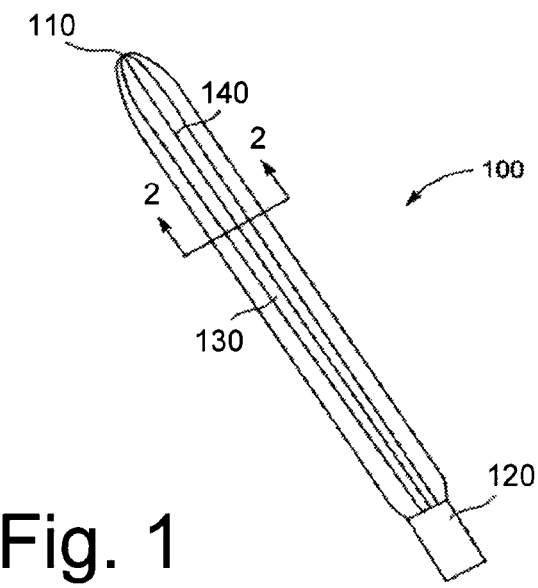
FIG. 1 is a schematic diagram of a wind turbine blade.
Figure 2:
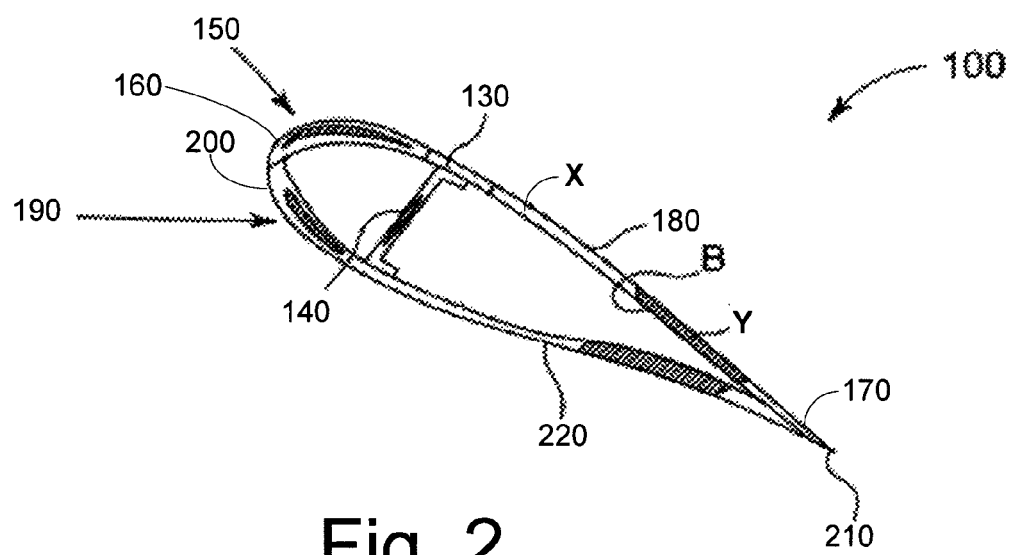
FIG. 2 is a side sectional view of a portion of the wind turbine blade of FIG. 1.

Referring now to the drawings, in which like numerals refer to like elements throughout the several views, FIGS. 1 and 2 show a wind turbine blade 100 as may be described herein. Generally described, the wind turbine blade 100 may be constructed of layers of an outer skin supported by a primary spar. Specifically, the wind turbine blade 100 may extend from a tip 110 to an opposing root 120. Extending between the tip 110 and the root 120 may be a spar cap 130 and a shear web 140. The shear web 140 may serve as the main structural support within the wind turbine blade 100. The spar cap 130 may be a glass portion running the length of the wind turbine blade 100 coincident with the shear web 140 so as to accommodate the tensile load on the wind turbine blade 100. The wind turbine blade 100 and the components thereof may have any size, shape, or configuration. Other components and other configurations also may be used herein.

As described above, the wind turbine blade 100 may be formed in shells. For example, a first shell 150 may extend from a first shell leading edge 160 to a first shell trailing ledge 170 and may define a suction surface 180. The first shell 150 may be bonded to a second shell 190. The second shell 190 may extend from a second shell leading edge 200 to a second shell trailing edge 210 and may define a pressure surface 220. The shells 150, 190 may be made out of fiber reinforced materials as well as core materials. Specifically, the layers of the shells 150, 190 may include a fiber-resin matrix. The core materials may include foam, balsa wood, engineered core materials, and the like. Other types of materials may be used herein.

In this example, the shells 150, 190 may be bonded together via an exothermic adhesive 230 to create a bond joint 240. Examples of suitable exothermic adhesives 230 may include a methyl methacrylate monomer (MMA), different types of cyanoacrylates, and similar types of materials. Generally described, an exothermic adhesive 230 will create heat during curing due to an exothermic chemical reaction upon the addition of a catalyst and the like. Many two part epoxies are exothermic at least in part. The layers of the shells 150, 190 and the exothermic adhesive 230 of the bond joint 240 may be cured in a conventional fashion.

A defect 245 in the bond joint 240 formed by the exothermic adhesive 230 may have an impact on the overall operation and lifetime of the wind turbine blade 100. Areas of concern for such a defect include the leading edges 160, 200; the trailing edges 70, 210; and about the spar cap 130. Each of these areas carries at least a portion of the tensile load on the blade 100 such that any bending of the fibers in these areas may reduce the strength of the fiber.

Figure 3:
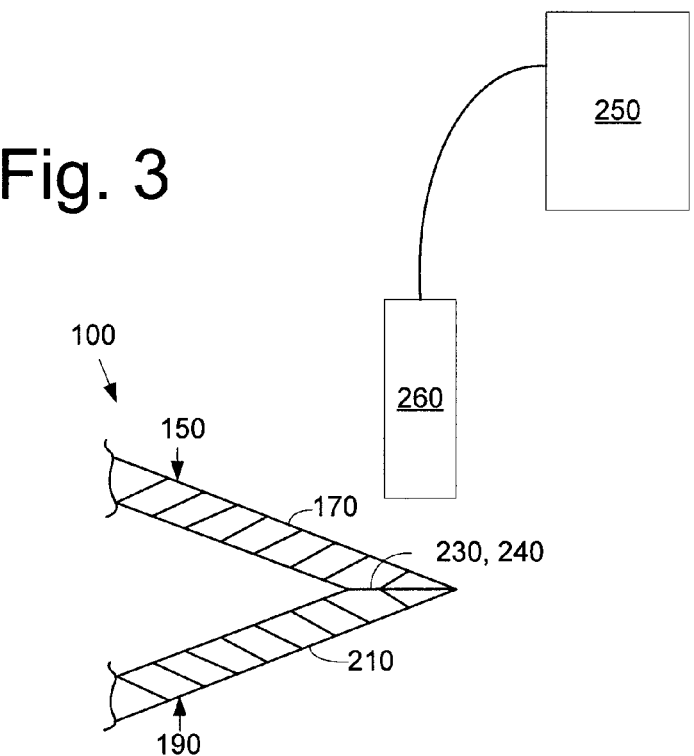
FIG. 3 is a schematic diagram of thermographic inspection system for use with a wind turbine blade having an exothermic adhesive bond joint as may be described herein.
Figure 4:
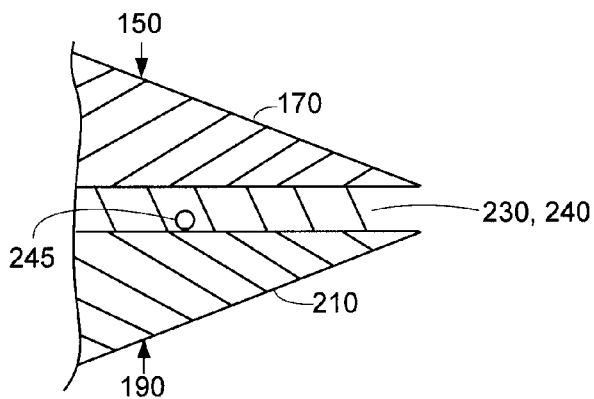
FIG. 4 is an expanded view of the wind turbine blade of FIG. 3 with the exothermic adhesive bond joint.

The wind turbine blade 100 thus may be inspected via a wind turbine blade thermographic inspection system 250 as may be described herein. The wind turbine blade thermographic inspection system 250 may be a type of non-destructive testing using thermography. Specifically, the wind turbine blade thermographic inspection system 250 may include an infrared camera 260 and the like as is shown in FIGS. 3 and 4. An example of an infrared camera 260 capable of providing the thermal images herein may be offered by FLIR Systems, by Fluke Corporation, by Omega Engineering, and by other entities. Any type of heat imaging and/or sensing device may be used herein. In addition to visual inspection of the thermal images, the thermal images produced by the infrared camera 260 may be processed by different types of software and/or algorithms to ensure overall compliance with predetermined parameters and the like. Other components and other configurations may be used herein.

Figure 5:
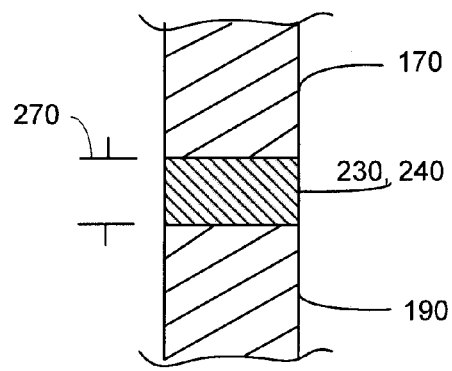
FIG. 5 is a further expanded view of the wind turbine blade of FIG. 3 with the exothermic adhesive bond joint.

In use, the wind turbine blade 100 may be assembled as described above with the exothermic adhesive forming the bond joint 240 between the shells 150, 190. As the exothermic adhesive 230 cures, heat may be released in a known manner. This heat may be visualized via the infrared camera 260 or other type of heat imaging device of the wind turbine blade thermographic inspection system 250. The wind turbine blade thermographic inspection system 250 thus may ensure the integrity of the bond joint 240. Moreover, the wind turbine blade thermographic inspection system 250 may verify the width 270 of the bond joint 240 at the leading edge 160, 200, the trailing edge 170, 210, and elsewhere as is shown in FIG. 5. These areas are often obscured by the foam, balsa, or other types of core materials that typically do not pass ultrasonic frequencies therethrough.

Further, the use of the exothermic adhesive 230 has the benefit of positioning a heat source exactly at the area of interest without the influence of an operator. The amount of heat generated must be controlled so as to avoid damage to the materials involved. The exothermic reaction provided by the exothermic adhesive 230 thus reduces the potential for an operator to overheat the area of interest. Specifically, the use of the wind turbine blade 100 and the wind turbine blade thermographic inspection system 250 provides a rapid and low cost inspection system with increased overall reliability and repeatability. Moreover, the inspection may be carried out in the field for "in situ" repairs where other types of testing may not be feasible.

Although the use of the exothermic adhesive 230 and the wind turbine blade thermographic inspection system 250 has been discussed in the context of the turbine blade bond joint 240 many other types of bond joints may be inspected herein. Any connection or bonding of two components may be evaluated herein.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

We claim:

1. A method of inspecting a bond joint, comprising:
    applying an exothermic adhesive to a first shell and/or a second shell;
    attaching the first shell to the second shell via the exothermic adhesive to create the bond joint;
    allowing the exothermic adhesive to cure;
    imaging the heat released by the exothermic adhesive along the bond joint to create a thermal image; and
    verifying, via the thermal image, a width of the bond joint between opposing surfaces of the first shell and the second shell.

2. The method of claim 1, wherein the bond joint comprises a turbine blade bond joint, wherein the step of applying the exothermic adhesive to the first shell and/or the second shell comprises applying the exothermic adhesive to a first turbine blade shell and/or a second turbine blade shell, and wherein the step of attaching the first shell to the second shell comprises attaching the first turbine blade shell to the second turbine blade shell.

3. The method of claim 1, further comprising the step of processing the thermal image, via software, to ensure compliance of the bond joint with one or more predetermined parameters.

4. The method of claim 2, wherein the step of attaching the first turbine blade shell to the second turbine blade shell comprises attaching a first shell leading edge to a second shell leading edge and attaching a first shell trailing edge to a second shell trailing edge.

5. The method of claim 2, wherein the step of attaching the first turbine blade shell to the second turbine blade shell comprises attaching a spar cap and a shear web.

6. The method of claim 1, wherein the step of imaging the heat released by the exothermic adhesive comprises imaging the heat released by the exothermic adhesive by an infrared camera.

7. The method of claim 6, wherein the step of imaging the heat released by the exothermic adhesive comprises maneuvering the infrared camera along the bond joint.

8. The method of claim 1, wherein the step of imaging the heat released by the exothermic adhesive comprises imaging a defect in the bond joint.

9. The method of claim 1, wherein the step of verifying the width of the bond joint comprises verifying the width of the bond joint between opposing surfaces of the first shell and the second shell along leading edges of the first shell and the second shell or along trailing edges of the first shell and the second shell.

10. A turbine blade inspection system, comprising:
    a plurality of turbine blades;
    each of the plurality of turbine blades comprising a bond joint between opposing surfaces of the turbine blade;
    the bond joint comprising an exothermic adhesive;
    a thermographic device;
    wherein the thermographic device images the heat released by the exothermic adhesive to create a thermal image to determine the integrity of the bond joint; and
    software operable to process the thermal image to ensure compliance of the bond joint with one or more predetermined parameters;
    wherein the one or more predetermined parameters comprises a width of the bond joint between the opposing surfaces.

11. The turbine blade inspection system of claim 10, wherein each of the plurality of turbine blades comprises a first shell and a second shell joined at the bond joint.

12. The turbine blade inspection system of claim 10, wherein each of the plurality of turbine blades comprises a spar cap and a shear web joined at the bond joint.

13. The turbine blade inspection system of claim 10, wherein the exothermic adhesive comprises a methyl methacrylate monomer, a cyanoacrylate, or a two-part epoxy.

14. The turbine blade inspection system of claim 10, wherein the thermographic device comprises an infrared camera.

15. The turbine blade inspection system of claim 10, wherein each of the plurality of turbine blades comprises a material selected from the group consisting of a composite material, a fiber-resin matrix, and a core material.

16. A turbine blade inspection system, comprising:
a plurality of turbine blades;
each of the plurality of turbine blades comprising a bond joint about a first shell and a second shell;
the bond joint comprising an exothermic adhesive;
an infrared camera;
wherein the infrared camera images the heat released by the exothermic adhesive to create a thermal image to determine the integrity of the bond joint; and
software operable to process the thermal image to ensure compliance of the bond joint with one or more predetermined parameters;
wherein the one or more predetermined parameters comprises a width of the bond joint between opposing surfaces of the first shell and the second shell.

17. The turbine blade inspection system of claim 16, wherein each of the plurality of turbine blades comprises a spar cap and a shear web joined at the bond joint.

18. The turbine blade inspection system of claim 16, wherein the exothermic adhesive comprises a methyl methacrylate monomer, a cyanoacrylate, or a two-part epoxy.

19. The turbine blade inspection system of claim 16, wherein each of the plurality of turbine blades comprises a composite material.

20. The turbine blade inspection system of claim 16, wherein each of the plurality of turbine blades comprises a fiber-resin matrix and a core material.

* * * * *